United States Patent

Hauenstein et al.

Patent Number: 5,284,942
Date of Patent: Feb. 8, 1994

[54] PROCESS FOR THE PREPARATION OF PERI-DICHALCOGENO POLYCYCLIC AROMATIC COMPOUNDS

[75] Inventors: Kurt Hauenstein, Unterendingen; Carl W. Mayer, Riehen, both of Switzerland

[73] Assignee: Ciba-Geigy Corporation, Ardsley, N.Y.

[21] Appl. No.: 849,556

[22] Filed: Mar. 11, 1992

[30] Foreign Application Priority Data

Mar. 15, 1991 [CH] Switzerland ............. 798/91

[51] Int. Cl.$^5$ ............. C07D 333/50; C07D 333/78; C07D 517/06; C07D 517/00
[52] U.S. Cl. ............. 540/1; 423/179; 423/508; 423/511; 549/4; 549/31
[58] Field of Search ............. 562/894; 549/31, 4; 560/10, 93, 56, 100, 102; 558/416, 418, 423, 411, 425; 556/413, 415, 418, 427, 432, 441, 489; 540/1; 423/179, 508, 511

[56] References Cited

U.S. PATENT DOCUMENTS 5,009,812  4/1991  Finter et al. ............. 524/412

OTHER PUBLICATIONS

T. Otsubo et al. Chemistry Letters pp. 315-316 (1987).
Palaniswamy et al. Chem. Abstract vol. 92(4):25135k (1980).
Syper et al. Synthesis, No. 5 pp. 439-442 (1984).
K. Balodis et al., Zhurnal Organicheskoi Khimii, 15 (2), pp. 391-393 (1979).
D. Sandman et al. Organometallics, 1, pp. 739-742 (1982).
B. Kruptsou et al., Chem. Abstract, 77(13):87350a (1972).

Primary Examiner—Richard L. Raymond
Attorney, Agent, or Firm—Kevin T. Mansfield; George R. Dohmann

[57] ABSTRACT

A process for the preparation of peri-dichalcogeno polycyclic aromatic compounds by preparing in a first step, in an amidic solvent, an alkali metal sulfide, selenide or telluride which, in a second step, is reacted with a peri-halogeno aromatic compound, which process comprises reacting in said first step an alkali metal base with elemental sulfur, selenium or tellurium at elevated temperature.

22 Claims, No Drawings

PROCESS FOR THE PREPARATION OF PERI-DICHALCOGENO POLYCYCLIC AROMATIC COMPOUNDS

The present invention relates to a process for the preparation of peri-dichalcogeno polycyclic aromatic compounds, which comprises producing, in a first step, an alkali metal chalcogenide by reacting sulfur, selenium or tellurium with an alkali metal base in the presence of an acid amide as solvent, and reacting said chalcogenide in a second step with a peri-halogeno aromatic compound.

Peri-chalcogeno polycyclic aromatic compounds are electron donors which, with electron acceptors, form crystalline radical ion salts with high electrical conductivity. To prepare peri-chalcogeno polycyclic aromatic compounds, it has been proposed by K. A. Balodis et al. in Zhurnal Organicheskoi Khimii, Vol. 15, No. 2, pages 391 bis 393 [(1979), English translation, Plenum Publishing Corporation, 1979] to react 5,6,11,12-tetrachlortetracene at elevated temperature with sodium diselenide which is obtained by the direct reaction of metallic sodium with selenium in dimethyl formamide as solvent. In this process, 5,6,11,12-tetraselenotetracene is obtained in a yield of 50%. In Organometallics, Vol. 1, pages 739 to 742 (1982), D. J. Sandman et al describe the same method for preparing 5,6,11,12-tetratellurotetracene (yield 13%). B. K. Kruptsov et al. describe in CA 77(13): 87350a that lithium reacts at 80° C. with dimethyl formamide.

The described methods have various drawbacks which prevent them from being carried out on an industrial scale. The reaction of alkali metals with amidic solvents does not permit unequivocal stoichiometric reaction ratios to be established, so that yields and product quality are not reproducable when using large batches. The reaction solutions are highly viscous owing to the formation of by-products, and the products are obtained in the form of very finely crystalline precipitates, thereby making it extremely difficult and time-consuming to separate them by filtration. In addition, the handling of large amounts of alkali metals is problematical and requires special safety measures.

It has now been found that peri-chalcogeno polycyclic aromatic compounds can be obtained in shorter reaction times in substantially higher yield and in good purity, avoiding the use of alkali metals and at fairly low temperature, by preparing the alkali metal chalcogens by reaction of alkali metal bases with elemental sulfur, selenium or tellurium in an amidic solvent. This is very surprising, as it was entirely unknown that alkali metal bases in such solvents are able to reduce elemental chalcogens virtually stoichiometrically to corresponding chalcogenides, and it was likewise unknown how this reaction proceeds.

Accordingly, the invention relates to a process for the preparation of peri-dichalcogeno polycyclic aromatic compounds by preparing in a first step, in an amidic solvent, an alkali metal sulfide, selenide or telluride which, in a second step, is reacted with a peri-halogeno aromatic compound, which process comprises reacting in said first step an alkali metal base with elemental sulfur, selenium or tellurium at elevated temperature.

Chalcogen denotes in this context the elements sulfur, selenium and tellurium.

The reaction temperature in the first step may conveniently be in the range from 30° C. to the reflux temperature of the solvent employed, preferably from 30° to 200° C. and, most preferably, from 50° to 150° C.

Preferred alkali metal bases are those of lithium, sodium and potassium, sodium being especially preferred. Suitable bases are typically the hydroxides, carbonates, hydrogen carbonates and alcoholates of primary, secondary and tertiary alkanols of preferably 1 to 18, more particularly 1 to 12 and, most preferably, 1 to 6 carbon atoms. In a preferred embodiment of the invention, the alkali metal alcoholates of $C_1$-$C_{18}$alkanols are used, most preferably corresponding sodium alcoholates. The sodium alcoholates are preferably derived from $C_1$-$C_6$alkanols. Sodium methylate is especially preferred. In a particularly preferred embodiment of the invention, the alkali metal bases are selected from the group consisting of NaOH, $NaHCO_3$, $Na_2CO_3$, $NaOCH_3$ and $KOC(CH_3)_3$.

The amidic solvents are preferably N-dialkylated carboxamides, the carboxylic acids from which they are derived preferably containing 1 to 6, most preferably 1 bis 3, carbon atoms; N-alkylated lactams and N-peralkylated amides of inorganic oxyacids, typically phosphoric acid or sulfuric acid. The alkyl groups at the N-atom preferably contain 1 to 4 carbon atoms, most preferably 1 or 2 carbon atoms. Typical examples of such solvents are N,N-dimethylformamide, N,N-diethylformamide, N,N-di-npropylformamide, N,N-dimethylacetamide, N-methylpyrrolidone, tetramethylurea and hexamethylphosphoric triamide. Preferred solvents are tetramethylurea, N-methylpyrrolidone and N,N-dimethylacetamide. It is especially preferred to use N,N-dimethylacetamide.

In the reaction of the elemental chalcogens sulfur, selenium and tellurium with the alkali metal bases, compounds of formula $M_2X_2$ are formed, wherein M is an alkali metal and X is sulfur, selenium or tellurium. The alkali metal bases and chalcogens are preferably used in stoichiometric proportions.

The reaction is conveniently carried out in an inert gas atmosphere and with the exclusion of moisture, as is also the second process step. A nitrogen or argon atmosphere is preferred.

The procedure in the first process step normally is that the alkali metal base and the chalcogen in the solvent are charged to the reactor and the mixture is then heated until the formation of the dialkali metal dichalcogenide is complete. The reaction times are in the order of half an hour to at most five hours, usually at most three hours. The second process step is then carried out directly afterwards.

The peri-halogeno aromatic compounds used in the second process step are preferably peri-bromo and, most preferably, peri-chloro aromatic compounds in which at least two adjacent peri-positions are halogenated. Peri-positions only occur in aromatic compounds with fused nuclei. Such compounds may be aromatic heterocyclic and, preferably, aromatic hydrocarbon, compounds which contain not fewer than 10 and up to 30 carbon atoms, preferably from 10 to 18 carbon atoms. Aromatic compounds are typically naphthalene, anthracene and tetracene.

In a preferred embodiment of the invention, the peri-halogeno aromatic compounds have the formula I

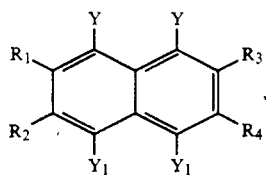

from which peri-chalcogeno compounds of formula II are prepared

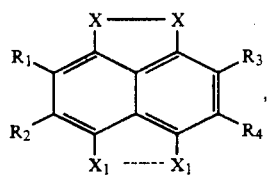

wherein Y is halogen, preferably Cl, $Y_1$ is H or halogen, preferably Cl, X is S, Se or Te, and $X_1$ is H, S, Se or Te, where $X_1$—$X_1$ represents a single bond except when $X_1$ is H, and $R_1$, $R_2$, $R_3$ and $R_4$ are each independently of one another H, $C_1$-$C_4$alkyl, $C_1$-$C_4$alkoxy, $C_1$-$C_4$alkylthio, halogen, preferably F, Cl and Br, CN, $CF_3$, $(CH_3)_3Si$, di($C_1$-$C_6$alkyl)N, CO($C_1$-$C_6$alkoxy) or OCO($C_1$-$C_6$alkoxy), or $R_1$ and $R_2$ or $R_3$ and $R_4$, each taken together, are the radical —CH=C($R_5$)—C($R_6$)=CH—, or $R_1$ and $R_2$, when taken together, are said radical, and $R_3$ and $R_4$, when taken together, are —CH=C($R_7$)—C($R_8$)=CH—, where $R_5$, $R_6$, $R_7$ and $R_8$ each independently have the meaning of $R_1$ to $R_4$.

$Y_1$ is preferably halogen, more particularly Cl, and $X_1$ is preferably S, Se or Te.

Especially preferred peri-halogeno aromatic compounds have the formulae Ia and Ib,

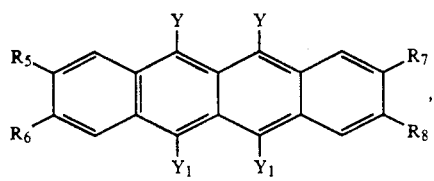

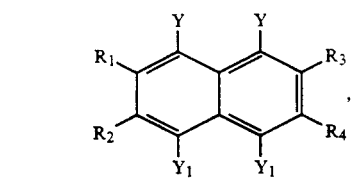

wherein Y is Cl and $Y_1$ is H or Cl, and $R_1$ to $R_4$ as well as $R_5$ to $R_8$ are each independently of one another H, F, Cl, $CF_3$, $CH_3$, $CH_3O$, $C_2H_5O$, $CH_3S$, $C_2H_5S$, $(CH_3)_3Si$, C(O)OCH$_3$ or C(O)OC$_2$H$_5$. Most preferably, $R_1$ to $R_4$ and $R_5$ to $R_8$ are H.

The compounds of formula Ia and Ib are known or they can be prepared by known methods.

The second step of the novel process is conveniently carried out direct after termination of the first step, without isolation of the alkali metal chalcogenide, in the same reaction medium. The reaction mixture may be cooled beforehand and, after addition of the peri-halogeno aromatic compound, heated again. However, the peri-halogeno aromatic compound may also be added to the hot reaction mixture. The peri-halogeno aromatic compound may conveniently be dissolved in a solvent or hot solvent or added to the reaction mixture without a solvent. At this time, the reaction mixture can also be diluted by adding a solvent. It is expedient to use the same solvent as in the first process step.

In a variant of the novel process, the procedure can also comprise charging the reactor with the alkali metal base and the elemental chalcogen together with the peri-halogeno aromatic compound in the solvent, heating the mixture and allowing the reaction to go to completion.

The reaction temperature may conveniently be from 30° C. to the boiling point of the solvent, preferably from 30° to 200° C. and, most preferably, from 50° to 150° C. The reaction times are normally from 15 minutes to about 2 hours.

The reactants are conveniently used in such proportions that at least 1 mol of alkali metal chalcogenide ($M_2X_2$) is present per 2 mol of adjacent peri-halogen atoms in 1 mol of aromatic compound. It has been found expedient to use an excess of alkali metal chalcogenide, conveniently up to mol, preferably up to 3 mol, of alkali metal chalcogenide per 2 mol of adjacent peri-halogen atoms in 1 mol of aromatic compound.

The peri-chalcogeno aromatic compounds are isolated in a manner known per se by filtration. It is therefore advantageous that coarse crystalline products are formed which can be easily separated. The products can be purified in conventional manner by washing off with solvents and, if necessary, recrystallisation and/or sublimation.

The peri-dichalcogeno aromatic compounds prepared by the process of this invention form radical ion salts with electron acceptors. These radical salts have high electrical conductivity (organic metals) and find utility as electrical conductors, typically as electrodes.

The invention is illustrated in more detail by the following Examples.

EXAMPLE 1

Preparation of 5,6,11,12-tetrathiotetracene

A 200 ml sulfonation flask is charged with 1.83 g (5 mmol) of 5,6,11,12-tetrachlorotetracene, 1.76 g (21 mmol) of sodium hydrogen carbonate, 0.8 g of sulfur and 75 ml of N,Ndimethylacetamide, and the mixture is refluxed for 1 hour under argon. The reaction mixture is then allowed to cool and the black precipitate is isolated by filtration. The precipitate is washed with N,N-dimethylacetamide, acetone, water and once more with acetone, and dried at 60° C. overnight under a high vacuum. The yield is 1.237 g (70.3%) and the purity of the title compound is 84%. The purity is determined spectroscopically in a solution of 1,2,4-trichlorobenzene with absorption band at 705 nm.

EXAMPLE 2

Preparation of 5,6,11,12-tetrathiotetracene

The procedure of Example 1 is repeated, but using 1.13 g (21 mmol) of sodium methylate as base and shortening the reaction time to 30 minutes. The yield is 77.8% and the spectroscopically determined purity of the title compound is 94.5%.

EXAMPLE 3

Preparation of 5,6,11,12-tetraselenotetracene

A 350 ml sulfonation flask is charged with 1.896 g (24 mmol) of selenium, 1.336 g (24 mmol) of sodium methylate and 50 ml N,N-dimethylacetamide, and the mixture is heated to reflux over 30 minutes and kept at this temperature for 1 hour. Then a hot solution of 1.83 g (5 mmol) of 5,6,11,12-tetrachlorotetracene in 100 ml of N,N-dimethylacetamide is tipped into the reddish-brown suspension, whereupon the reaction mixture immediately turns green. The reaction mixture is refluxed for another 20 minutes and then cooled to 50° C. The crystalline black precipitate is isolated by filtration, washed with 50 ml of N,N-dimethylacetamide and then with 400 ml of water and 400 ml of acetone. The residue is dried overnight at 60° C. under a high vacuum, giving 2.36 g (87.4%) of crude product. The spectroscopically determined purity of the title compound (absorption band at 712 nm) is greater than 97%.

EXAMPLE 4

Preparation of 5,6,11,12-tetraselenotetracene

With stirring, 0.948 g (12 mmol) of selenium, 0.668 g (12 mmol) of sodium methylate and 25 ml of N-methylpyrrolidone are heated under argon from room temperature to 140° C. and stirred for a further hour. A hot solution of 140° C. of 0.915 g (2.5 mmol) of 5,6,11,12-tetrachlorotetracene in 50 ml N-methylpyrrolidone is then tipped into the reddish-brown suspension. After 20 minutes, the batch is cooled to room temperature and the precipitate is washed with 25 ml of cold N-methylpyrrolidone, 2×100 ml of water and 2×100 ml of acetone and then dried at 40° C. under a high vacuum. Yield: 0.959 g (71%) of crude product. The purity of the title compound is 93%.

EXAMPLE 5

Preparation of 5,6,11,12-tetraselenotetracene

The procedure of Example 4 is repeated, using tetramethylurea as solvent. Yield: 1.35 g of crude product. The purity of the title product is 79%.

EXAMPLE 6

Preparation of 5,6,11,12-tetraselenotetracene 1.738 g (22 mmol) of selenium, 2.655 g (23 mmol) of potassium tert-butylate and 50 ml of dimethyl acetamide are heated under argon for 30 minutes to 145° C. A solution of 1.83 g (5 mmol) of 5,6,11,12-tetrachlorotetracene in 100 ml of dimethyl acetamide is then tipped into the reddish-brown suspension, and the mixture is then stirred at 155° C. for 20 minutes. The reaction mixture is cooled to 50° C. and the black precipitate is filtered with suction, washed with 50 ml of dimethyl acetamide, 400 ml of water and 2×100 ml of acetone, and dried at 50° C. under a high vacuum. Yield: 1.59 g (58.9%) of crude product. The purity of the title compound is 97%.

EXAMPLE 7

Preparation of 5,6,11,12-tetraselenotetracene 0.948 g (12 mmol) of selenium, 1.008 g (12 mmol) of $NaHCO_3$ and 1 ml of water are stirred in dimethyl acetamide for 2 hours at 130° C. under argon. Then a hot solution of 130° C. of 0.915 g (2.5 mmol) of 5,6,11,12-tetrachlorotetracene in 50 ml of dimethyl acetamide is added and the batch is stirred for another 3 hours. The batch is then cooled and the precipitate is filtered with suction, washed with 25 ml of dimethyl acetamide, 100 ml of water and 100 ml of acetone, and dried at 50° C. under a high vacuum. Yield: 0.887 g (65.7%) of crude product. The purity of the title compound is 69%.

EXAMPLE 8

5,6,11,12-tetraselenotetracene 0.948 g (12 mmol) of selenium, 0.636 g (8 mmol) of sodium carbonate, 25 ml of dimethyl acetamide and 3 ml of water are heated to 140° C. under argon and the mixture is stirred for 1 hour at this temperature. Then a hot solution of 130° C. of 0.915 g (2.5 mmol) of 5,6,11,12-tetrachlorotetracene in 50 ml of dimethyl acetamide is tipped in and the batch is stirred for another 4 hours at 140° C. After cooling to room temperature, the black precipitate is isolated by filtration, washed with 25 ml of dimethyl acetamide, 100 ml of water and 100 ml of acetone, and dried at 50° C. under a high vacuum. Yield: 0.84 g (62%) of crude product. The purity of the title compound is 58%.

EXAMPLE 9

5,6,11,12-tetraselenotetracene 480 mg (12 mmol) of NaOH are dissolved in 1 ml of water and the solution is added to a suspension of 0.948 g (12 mmol) of selenium in 25 ml of dimethyl acetamide. The mixture is then stirred for 1 hour at 140° C. Then a hot solution of 130° C. of 0.915 g (2.5 mmol) of 5,6,11,12-tetrachlorotetracene in 50 ml of dimethyl acetamide is tipped into the above mixture, and the batch is stirred for another 4 hours at 150° C. under argon. After cooling to 50° C., the black precipitate is isolated by filtration, washed with 30 ml of dimethyl acetamide, 200 ml of water and 200 ml of acetone, and dried at 50° C. under a high vacuum. Yield: 1.137 g (84%) of crude product. The purity of the title compound is 88%.

EXAMPLE 10

Preparation of 2-fluoro-5,6,11,12-tetraselenotetracene 0.948 g (12 mmol) of selenium, 0.668 g (12 mmol) of sodium methylate and 25 ml of dimethyl acetamide are heated for 30 minutes under argon to 150° C., and the mixture is stirred for 1 hour at this temperature. Then a hot solution of 150° C. of 2.5 mmol of 2-fluoro-5,6,11,12-tetraselenotetracene in 50 ml of dimethyl acetamide is tipped into the above mixture and the batch is stirred for 20 minutes at 150° C. After cooling to room temperature, the black precipitate is isolated by filtration, washed with 20 ml of dimethyl acetamide, 200 ml of water and 200 ml of acetone, and dried at 50° C. under a high vacuum. Yield: 1.142 g (81%) of crude product. The purity of the title compound is 86%.

EXAMPLE 11

Preparation of 1,4,5,8-tetraselenonaphthalene 0.948 g (12 mmol) of selenium, 0.668 g (12 mmol) of sodium methylate and 25 ml of dimethyl acetamide are heated for 30 minutes under argon to 150° C., and the mixture is stirred for 1 hour at this temperature. Then a hot solution of 140° C. of 2.5 mmol of 1,4,5,8-tetrachloronaphthalene in 50 ml of dimethyl acetamide is tipped into the above mixture and the batch is stirred for 22 hours at 150° C. After cooling to room temperature, the black precipitate is isolated by filtration, washed with 20 ml of dimethyl acetamide, 200 ml of water and 200 ml of acetone, and dried at 50° C. under a high vacuum. Yield: 0.953 g (86.6%) of crude product. The purity of the title compound is almost 100%.

EXAMPLE 12

Preparation of 5,6,11,12-tetratellurotetracene

The procedure of Example 3 is repeated, using tellurium in place of selenium. The yield of crude product and the purity of the title compound substantially match the particulars given in Example 3.

What is claimed is:

1. A process for the preparation of a compound of the formula $M_2X_2$, wherein M is an alkali metal and X is a chalcogen selected from the group consisting of sulfur, selenium or tellurium, which process comprises reacting an alkali metal containing base with the elemental chalcogen, in an amidic solvent, at an elevated reaction temperature.

2. A process according to claim 1, wherein the reaction temperature is from 30° C. to the reflux temperature of the solvent used.

3. A process according to claim 2, wherein the reaction temperature is from 30° to 200° C.

4. A process according to claim 1, wherein the alkali metal of the alkali metal containing base is selected from the group consisting of lithium, sodium and potassium.

5. A process according to claim 1, wherein the alkali metal containing base is selected from the group consisting of the alkali-metal hydroxides, carbonates, hydrogen carbonates and alcoholates of primary, secondary and tertiary alkanols.

6. A process according to claim 5, wherein the alkanols contain from 1 to 18 carbon atoms.

7. A process according to claim 5, wherein the alcoholate is a sodium alcoholate.

8. A process according to claim 7, wherein the sodium alcoholate is the sodium alcoholate of a $C_1$-$C_6$alkanol.

9. A process according to claim 1, wherein the alkali metal containing base is sodium methylate.

10. A process according to claim 1, wherein the amidic solvent is selected from the group consisting of N-dialkylated carboxamides, N-alkylated lactams and N-peralkylated amides of inorganic oxyacids.

11. A process according to claim 10, wherein the amidic solvent is N,N-dimethylacetamide.

12. A process of claim 1 wherein the alkali metal containing base and the chalcogen are reacted in stoichiometric proportions, in the presence of an inert atmosphere, with the exclusion of moisture, at a temperature of from 50° C. to 150° C.

13. A process of claim 1 which comprises an additional step wherein the compound of formula $M_2X_2$ is reacted with a peri-halogeno polycyclic aromatic compound to form a peri-chalcogeno polycyclic aromatic compound.

14. A process of claim 13 wherein the alkali metal containing base and the elemental chalcogen are reacted in the presence of the peri-halogeno polycyclic aromatic compound.

15. A process according to claim 13, wherein the peri-halogeno aromatic compound is a peri-bromo or peri-chloro compound.

16. A process according to claim 13, wherein the peri-halogeno aromatic compound is an aromatic heterocyclic or aromatic hydrocarbon compound which contains not fewer than 10 and up to 30 carbon atoms.

17. A process according to claim 13, wherein the peri-halogeno aromatic compound has the formula I

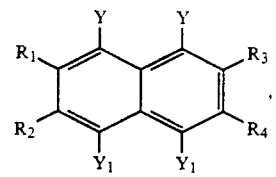

from which a peri-chalcogeno compound of formula II is prepared

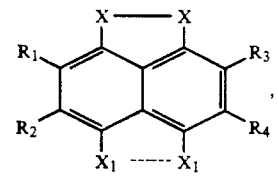

wherein Y is halogen, $Y_1$ is H or halogen, X is S, Se or Te, and $X_1$ is H, S, Se or Te, where $X_1$—$X_1$ represents a single bond except when $X_1$ is H, and $R_1$, $R_2$, $R_3$ and $R_4$ are each independently of one another H, $C_1$-$C_4$alkyl, $C_1$-$C_4$alkoxy, $C_1$-$C_4$alkylthio, halogen, CN, $CF_3$, $(CH_3)_3Si$, $di(C_1$-$C_6alkyl)N$, $CO(C_1$-$C_6alkoxy)$ or $OCO(C_1$-$C_6alkoxy)$, or $R_1$ and $R_2$ or $R_3$ and $R_4$, each taken together, are the radical —CH=C($R_5$)—C($R_6$)=CH—, or $R_1$ and $R_2$, when taken together, are said radical, and $R_3$ and $R_4$, when taken together, are —CH=C($R_7$)—C($R_8$)=CH—, where $R_5$, $R_6$, $R_7$ and $R_8$ each independently have the meaning of $R_1$ to $R_4$.

18. A process according to claim 17, wherein Y or $Y_1$ or both are Cl.

19. A process according to claim 17, wherein the peri-halogeno aromatic compound has the formula Ia or Ib, (Ia)

(Ib)

wherein Y is Cl and $Y_1$ is H or Cl, and $R_1$ to $R_4$ as well as $R_5$ to $R_8$ are each independently of one another H, F, Cl, $CF_3$, $CH_3$, $CH_3O$, $C_2H_5O$, $CH_3S$, $C_2H_5S$, $(CH_3)_3Si$, $C(O)OCH_3$ or $C(O)OC_2H_5$.

20. A process according to claim 19, wherein $R_1$ to $R_4$ and $R_5$ to $R_8$ are H.

21. A process according to claim 13, wherein the reaction temperature is from 30° C. to the boiling temperature of the solvent.

22. A process according to claim 13, wherein the reactants are used in such proportions that at least 1 mol of alkali metal chalcogenide $M_2X_2$ is present per 2 mol of adjacent peri-halogen atoms in 1 mol of aromatic compound.

* * * * *